United States Patent [19]

Harrigan

[11] 4,237,872
[45] Dec. 9, 1980

[54] EXTERNAL CARDIAC RESUSCITATION AID

[76] Inventor: Roy M. Harrigan, Bromley Mountain Rd., Manchester, Vt. 05254

[21] Appl. No.: 34,646

[22] Filed: Apr. 30, 1979

Related U.S. Application Data

[62] Division of Ser. No. 908,467, May 22, 1978, which is a division of Ser. No. 688,348, May 20, 1976, Pat. No. 4,095,590.

[51] Int. Cl.³ .............................................. A61H 1/00
[52] U.S. Cl. ................................................. 128/24 R
[58] Field of Search .................... 128/24 R, 28, 50–54

[56] References Cited

U.S. PATENT DOCUMENTS

| | | | |
|---|---|---|---|
| 3,219,031 | 11/1965 | Rentsch, Jr. | 128/51 |
| 3,351,052 | 11/1967 | Hewson | 128/145.8 X |
| 3,489,140 | 1/1970 | Mullikin | 128/51 |

*Primary Examiner*—John D. Yasko
*Attorney, Agent, or Firm*—Donald A. Kettlestrings

[57] ABSTRACT

Portable apparatus is provided for use by a rescuer in administering cardiopulmonary resuscitation to a patient or for use as a training aid in the application of cardiopulmonary resuscitation. A light weight, inflatable, fluid-filled, foam or other resilient cushion has a pressure gauge attached thereto, and the cushion is placed on the patient's chest. Force is applied by the rescuer onto the cushion and the pressure gauge displays the force applied so as to enable the rescuer to observe and control the force being applied to the patient's chest. A timer may also be provided with the pressure gauge to enable the rescuer to properly time the application and release of force to the patient's chest.

8 Claims, 41 Drawing Figures

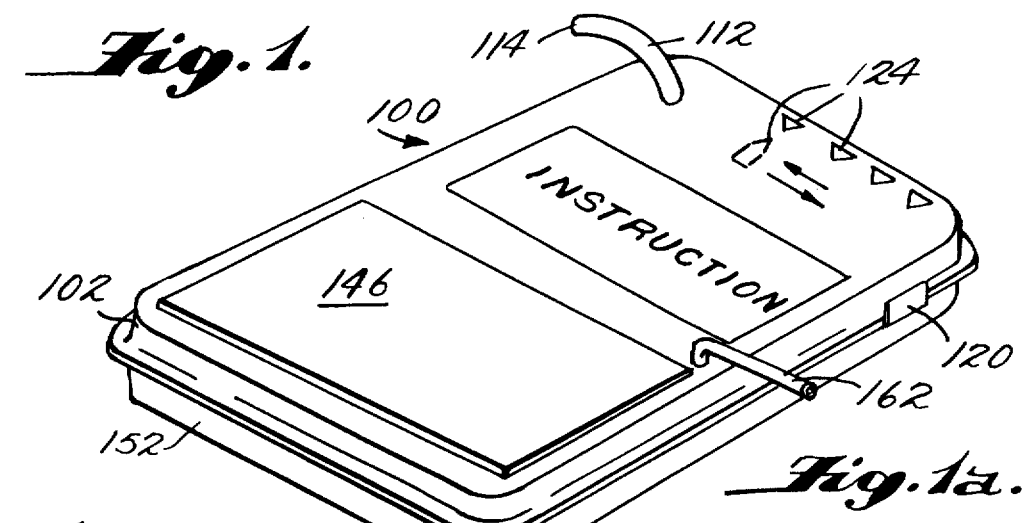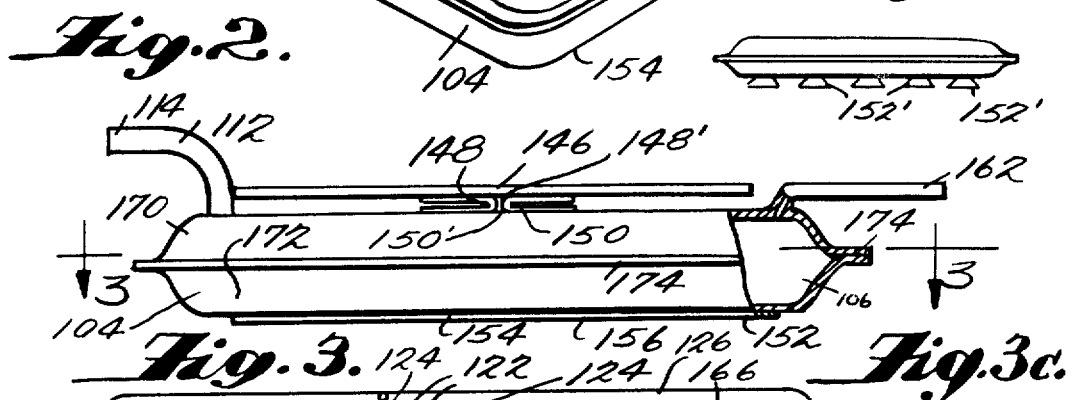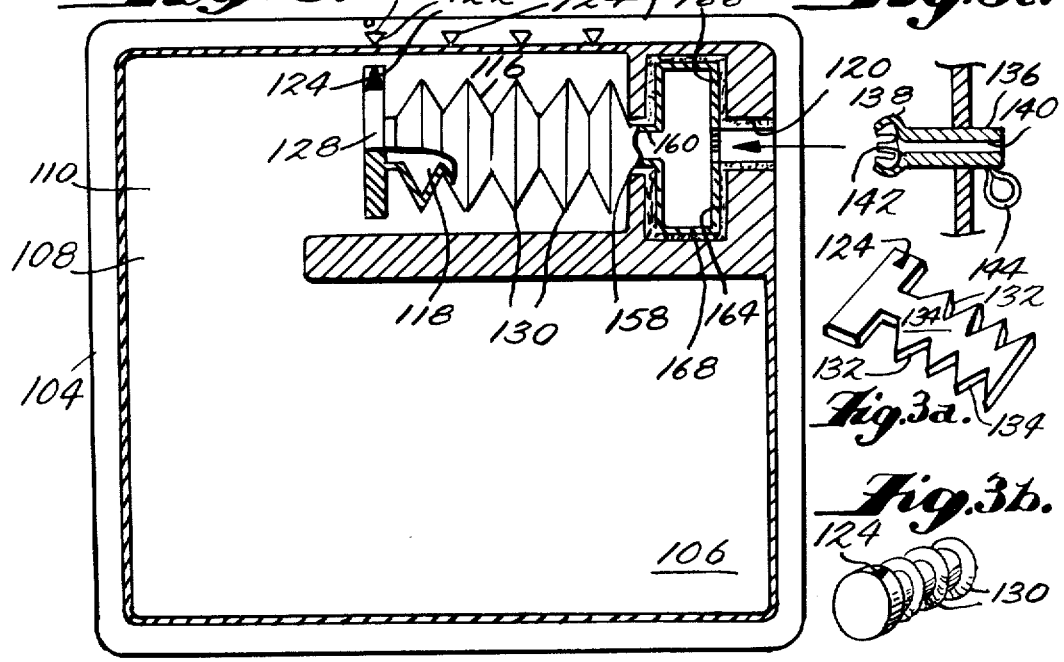

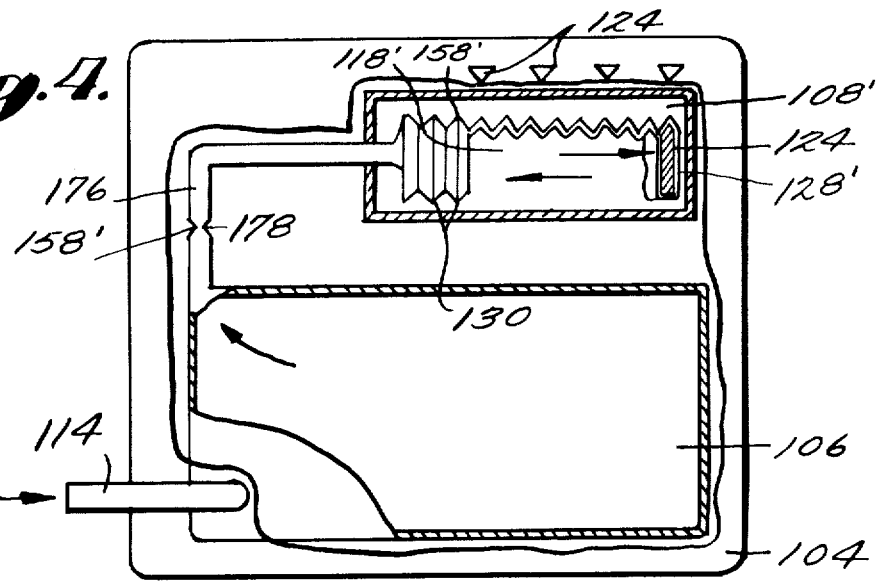
Fig. 4.
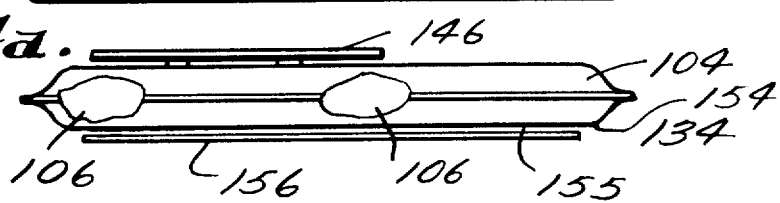
Fig. 4a.
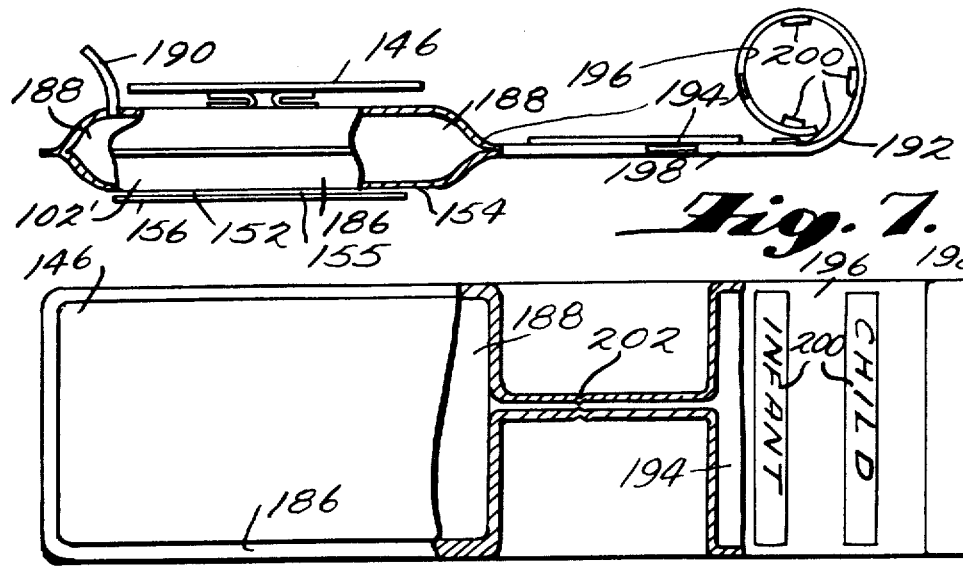
Fig. 6.
Fig. 7.

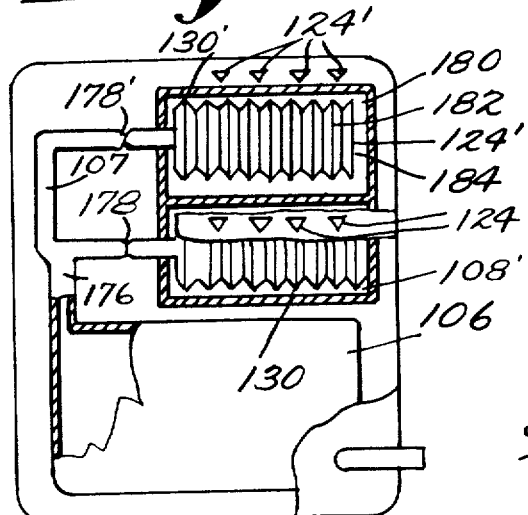
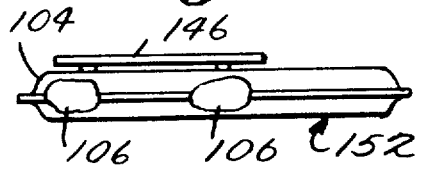
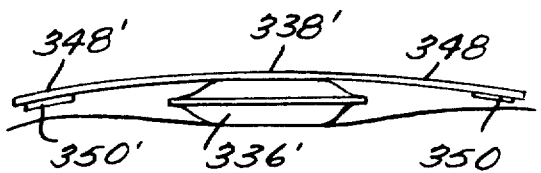
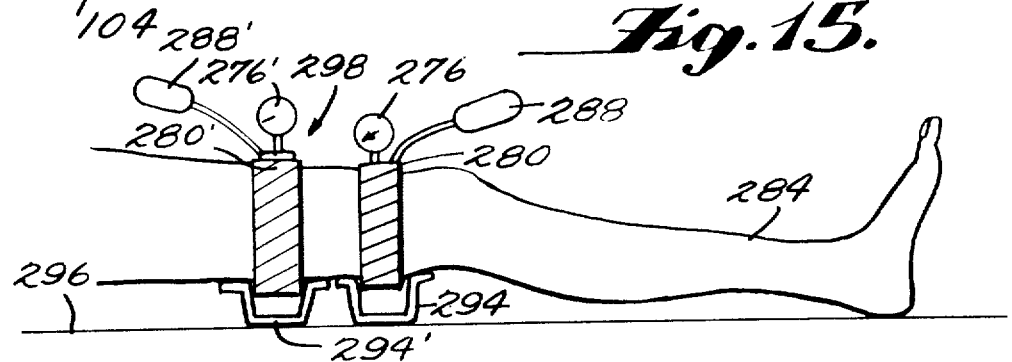
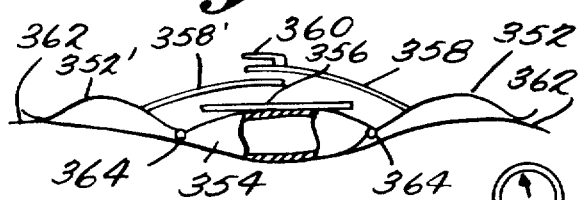
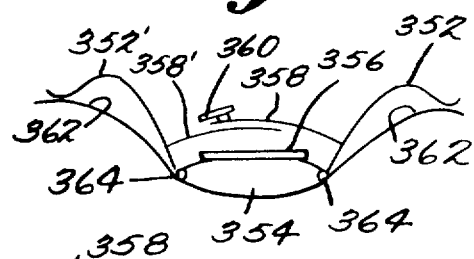
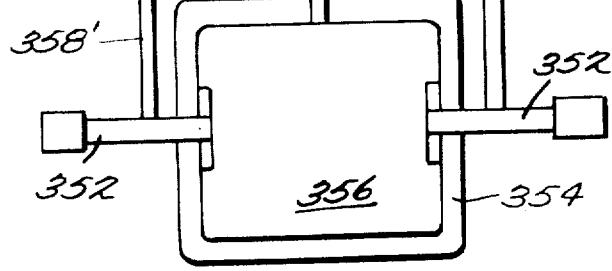

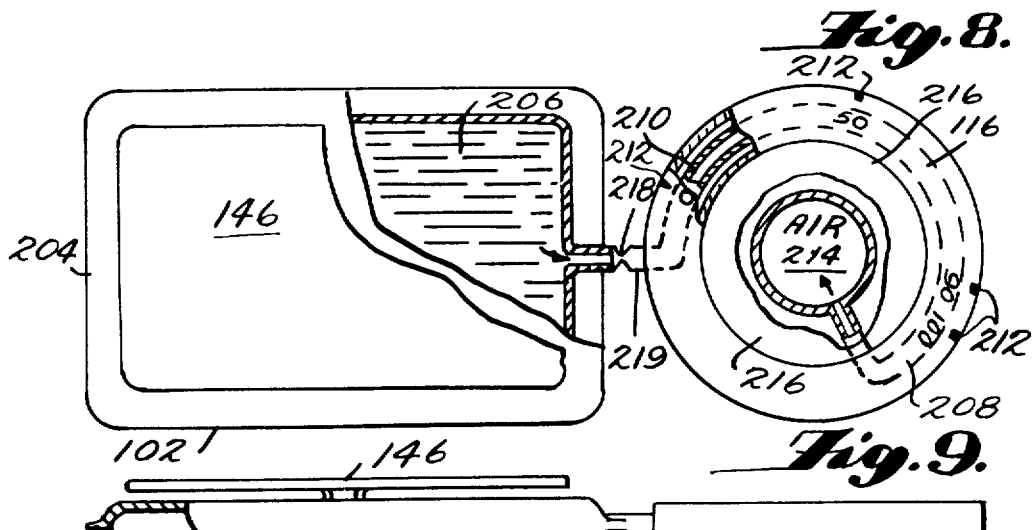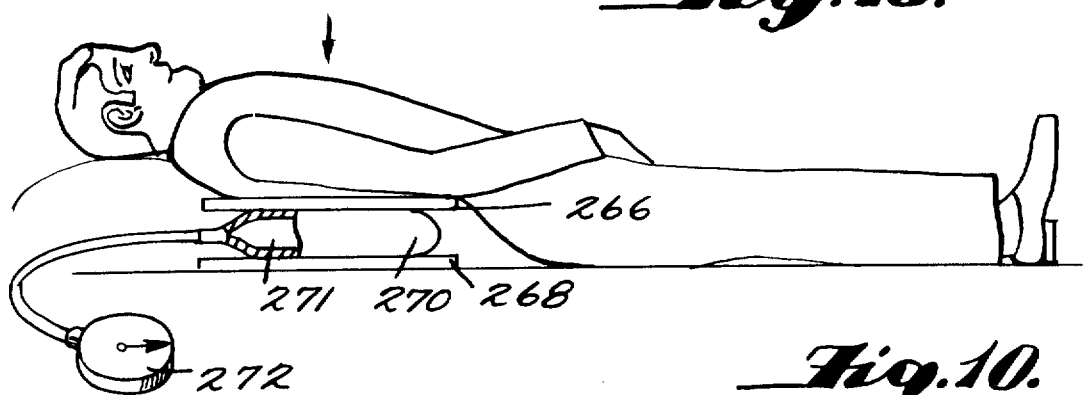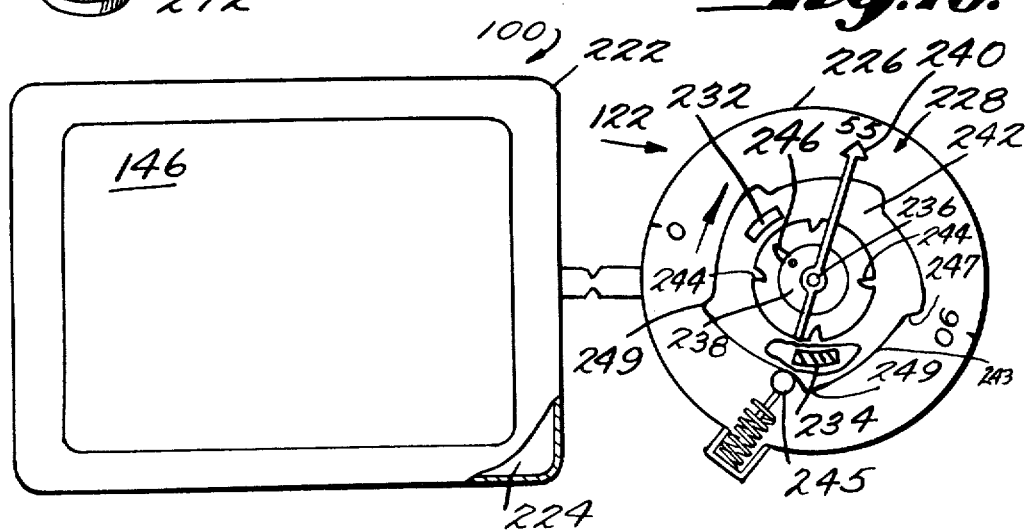

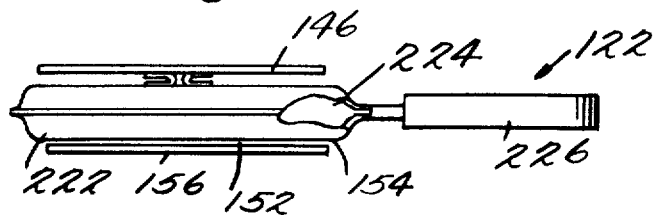
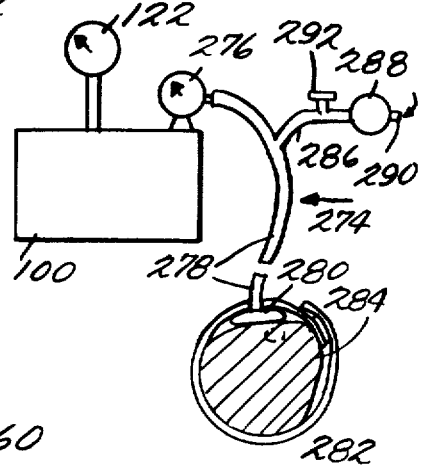
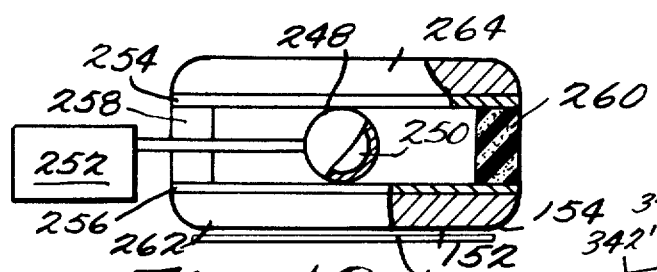
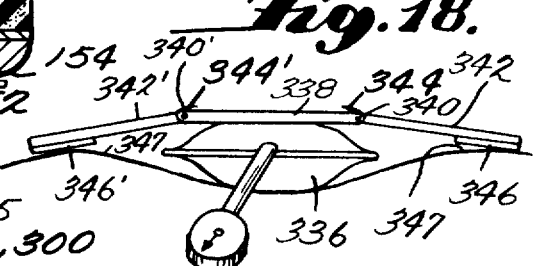
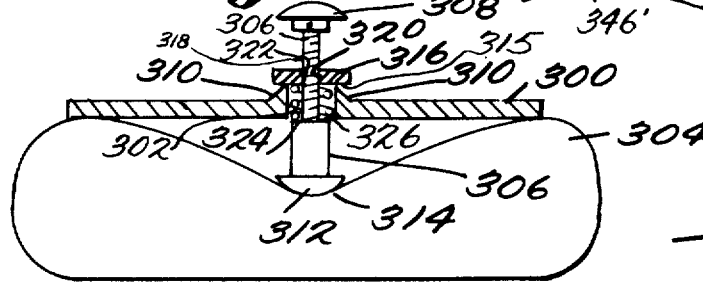
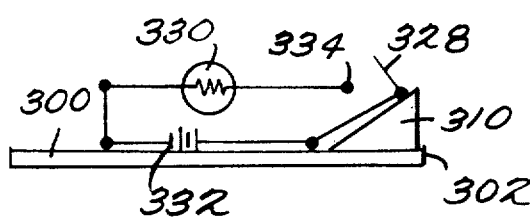
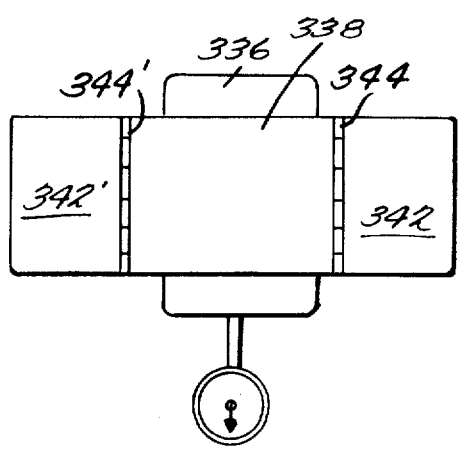

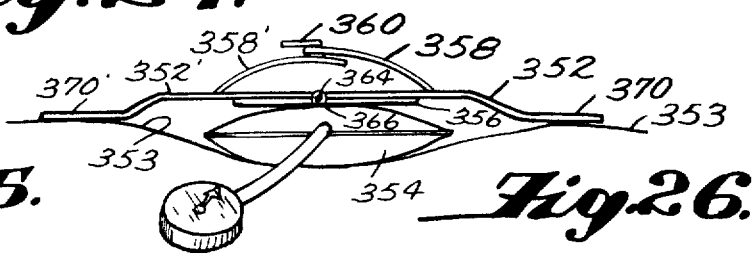
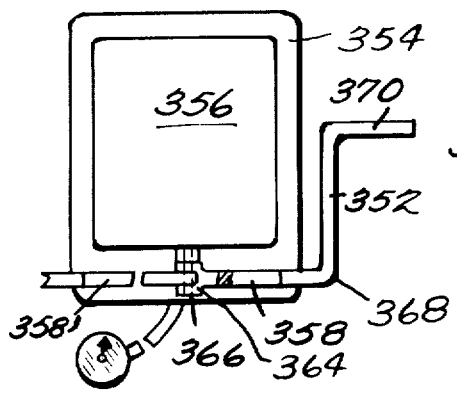
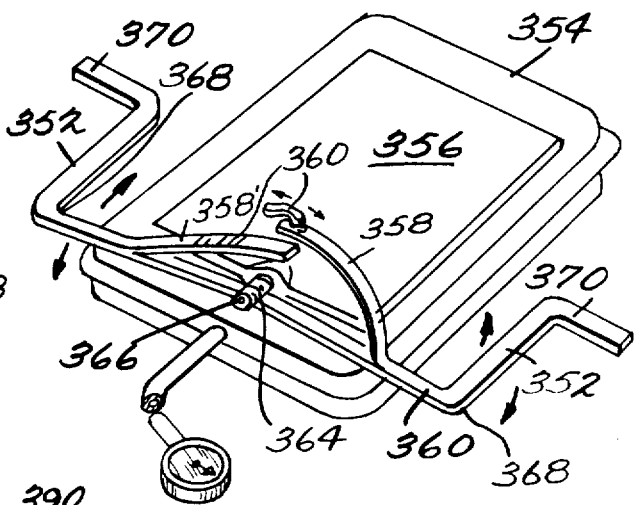
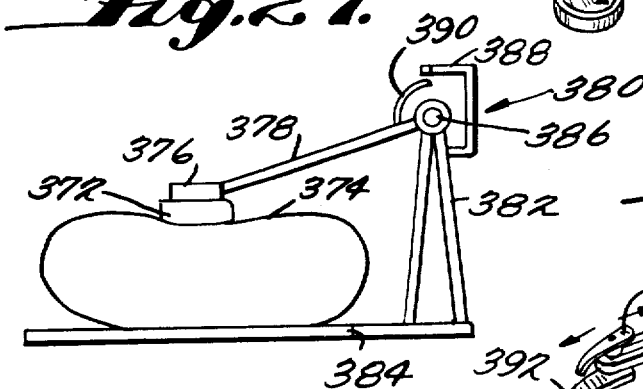
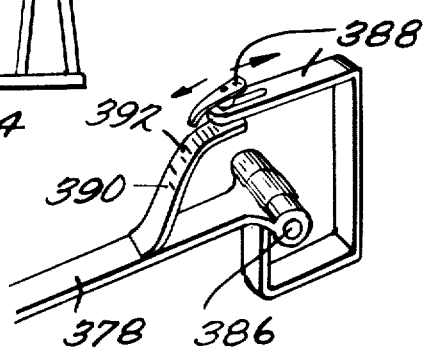

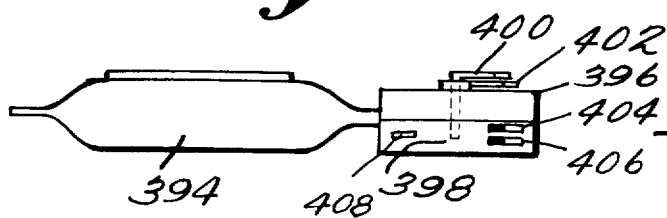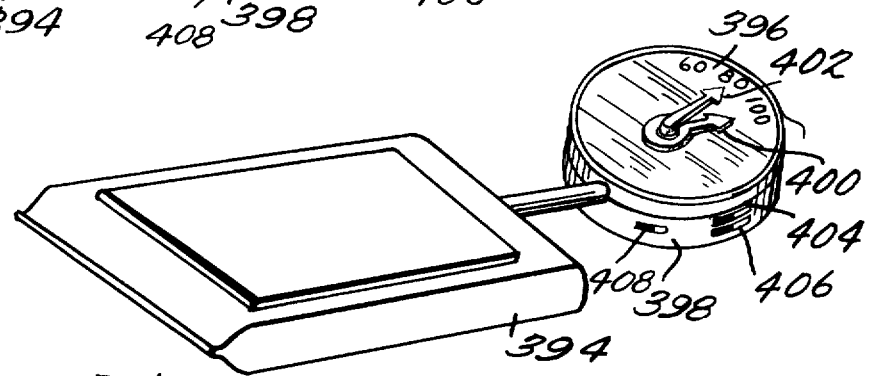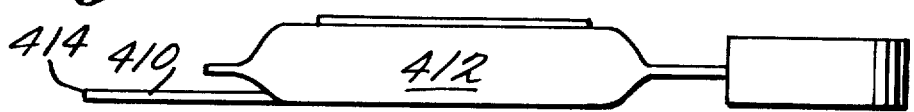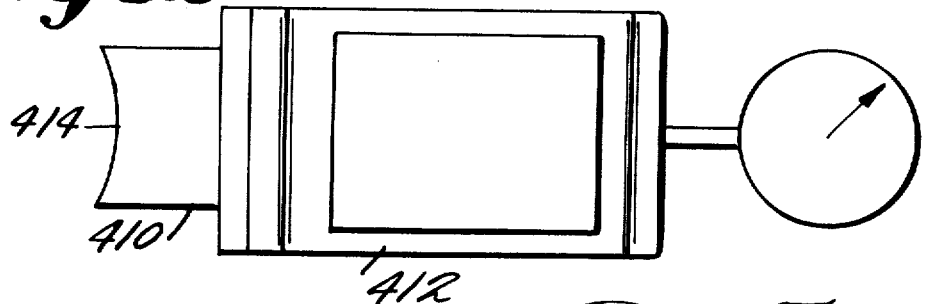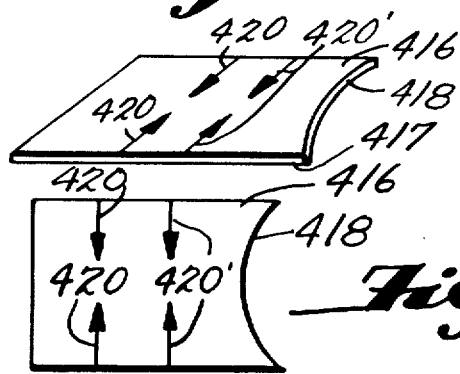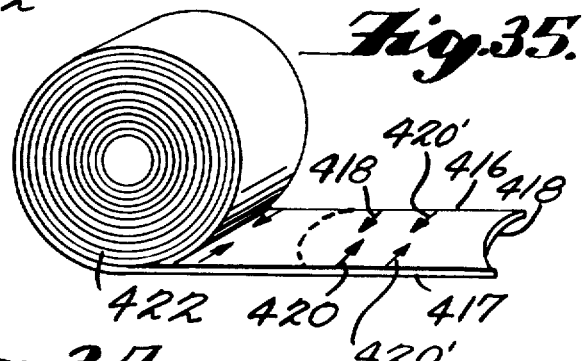

EXTERNAL CARDIAC RESUSCITATION AID

CROSS-REFERENCE TO RELATED APPLICATIONS

This is a division of application Ser. No. 908,467, filed May 22, 1978, which was a division of application Ser. No. 688,348, filed May 20, 1976, now U.S. Pat. No. 4,095,590.

This invention relates to apparatus for use by a rescuer in administering cardiopulmonary resuscitation to a patient or for use as a training aid in the application of cardiopulmonary resuscitation. More particularly, the present invention relates to apparatus for placement on the patient's chest to receive and to transmit to the patient manual force or pressure applied to the apparatus by the rescuer. A pressure gauge is preferably provided for enabling the rescuer to accurately control and time the force applied to the patient's chest when administering external cardiac resuscitation.

When the heart is stopped as a result of injury, poisoning, electric shock, heart attack or other causes, circulation sufficient to maintain life may be maintained by the rhythmic application and release of the correct amount of force or pressure to the patient's chest. In adult males the correct force is approximately ninety (90) pounds applied and removed at the rate of sixty (60) cycles per minute. For adolescents, the correct force is approximately fifty-five (55) pounds applied and released at the rate of eighty (80) cycles per minute. If too little force is applied, the patient's blood circulation will not be sufficient to prevent brain damage or even death. On the other hand, if the force applied is too great, broken ribs, punctured lungs and other potentially fatal damage may result. In addition, application and release of even the proper pressure or force will not be optimally effective unless the force is applied and released at the proper rate. Also, application of the proper pressure or force on too small or concentrated an area of the chest can result in broken ribs and other damage. For example, if the knuckles of the rescuer's hand are pressing on the victim's ribs severe injury can result. If the force is not applied evenly but applied in quick jabs, the likelihood of injury is also increased.

External cardiac compression is normally combined with mouth-to-mouth resuscitation for best results. This combination constitutes cardiopulmonary or heat-lung resuscitation. The most effective technique requires two rescuers, one to apply a continuous and uninterrupted series of compressions to the patient's chest and one to interpose a breath to the patient between every fifth and sixth compression of the patient's sternum or heart by the other rescuer. This avoids pauses in the patient's blood circulation and provides full lung inflations twelve (12) times per minute so as to assure optimum oxygenation, blood pressure and blood flow.

Frequently, cardiopulmonary resuscitation must be performed without assistance. In this instance, the single rescuer should compress the patient's heart fifteen (15) times at a rate of one (1) per second and then inflate the patient's lungs twice, mouth-to-mouth. This cycle should then be repeated. while this does not provide the optimum ventilation and circulation, it is the best procedure until a second rescuer is present.

It is, therefore, an object of this invention to provide an apparatus and method whereby the force applied during external cardiac resuscitation may be observed and accurately controlled by the person administering such aid.

It is a further object of this invention to provide an inexpensive, compact and portable device which will indicate the amount of pressure or force applied by a rescuer to the patient's chest during external cardiac resuscitation.

It is also an object of this invention to provide a simply constructed and inexpensive pressure or force distribution device which optionally may not have the pressure or force measuring and indicating feature.

It is another object of this invention to provide one or more of the above-described devices with a timer to insure that the rescuer will use the appropriate rhythm in the application of external cardiac resuscitation.

It is a further object of the invention to provide apparatus for measuring the depth of depression of the patient's sternum during external cardiac resuscitation.

Still another object of the invention provides apparatus for limiting the extent of depression of the patient's sternum during external cardiac resuscitation.

It is a further object of the invention to provide apparatus for counting the number of applications of pressure or force by the rescuer to the patient's chest.

Another object of the invention is to provide apparatus for measuring the patient's blood pressure so that the adequacy of resuscitation may be determined.

It is a further object of the invention to provide certain of the above-mentioned devices with an adhesive backing or other means so that the device will not slide from the proper position on the patient's chest.

Additional objects and advantages of the invention will be set forth in part in the description which follows, and in part will be obvious from the description or may be learned by practice of the invention. The objects and advantages are realized and attained by means of the instrumentalities and combinations particularly pointed out in the appended claims.

To achieve these and other objects, the present invention provides for an inflatable or other cushion structure of heavy vinyl or other suitable material approximately two inches wide, four inches long, and two inches high (when inflated) having a pressure or force indicating device, such as a pressure gauge, associated therewith. The structure is inflated by outh through a suitable inflation valve, such as are found on air mattresses or the structure can be permanently filled with a liquid. The gauge may be calibrated to indicate the pressure applied to a patient by placing the inflatable structure on a spring weight scale and applying various pressures (especially in the range required for external cardiac resuscitation) to the structure. These pressures registered by the spring weight scale are then recorded onto the face of the pressure gauge indicator. In experiments it has been found that a pressure of eight (8) pounds per square inch is representative of a downward force on the inflatable structure of ninety (90) pounds. This, however, is dependent on the size of the structure and other factors. The gauge may also be calibrated to indicate force.

In use, the above described external cardiac resuscitation aid is inflated by mouth and placed onto the patient's chest over the lower sternum, and pressure or force is applied to the patient's chest through the device. The rescuer observes the gauge while he applies manual chest compression (about once per second) to be sure that the proper pressure or force is attained.

In another embodiment of the invention, a rigid, flat, platelike member is attached to the upper portion of the inflatable cushion for enhancing even distribution of pressure or force to the patient's chest and to provide a more accurate pressure or force reading. The use of such a flat member prevents errors in pressure caused by hydraulic effects of various hand sizes and hand positions on the cushion.

A further embodiment of the invention provides for a timing device associated with the pressure gauge to enable the rescuer to maintain the proper rhythm. Various adjustable timing devices and indicators can be used, such as audible, visual or even tactile signals, as examples. Electronic or othe timing means and even a compact metronome device could be used.

The timer may be an integral part of the pressure gauge. The pressure gauge may be designed so that an appropriate time interval, e.g. one-half ($\frac{1}{2}$) second, is required for the pressure or force indicator pointer to relax from ninety (90) pounds to zero. Ideally, this timing feature is adjustable to suit different circumstances and different resuscitation rates. For example, the guage is preferably designed so that the indicator pointer will relax from a lower than ninety poured reading to zero in less than one-half second and from a greater than ninety pound reading to zero in more than one-half second. This enables the rescuer to maintain the proper rhythm for adults and children. The gauge automatically sets the proper rhythm for each pressure or force. For example, the indicator pointer will relax from a fifty five (55) pounds reading to zero in less than one-half second to create a rate of eighty (80) cycles per minute while a ninety (90) pounds pressure results in a ratio of sixty (60) cycles per minute.

The resiliency of the cushion is also a valuable feature of the invention. This resiliency tends to reduce the chances of damage or injury to the patient when administering cardiopulmonary resuscitation (CPR) by virtue of the fact that it provides for an even distribution of pressure or force to the patient's chest. The use of a rigid, platelike member attached to the upper portion of the cushion further enchances this even distribution.

In addition, the cushion tends to absorb the harmful effects of improperly applied CPR, such as sharp jabs rather than even, regular compressions. In fact, one embodiment of the invention consists simply in an inflatable pillow or cushion or other similarly shaped structure of suitable material such as foam rubber or plastic for the application of CPR. Such a device would be of value even though it did not have the pressure or force sensing and indicating means and other features described above. However, it could include these additional features or any combination thereof, including the use of the timing means.

Further improvement to the above-described embodiments is the provision of a pressure sensitive adhesive surface, such as medical adhesive tape or suction cups on the bottom of the resilient and/or inflatable cushion. With such adhesive characteristics, the rescuer need only locate the proper position for the device and apply it to the patient's chest. Then, should the rescuer have to stop the CPR for a limited interval because of moving or transporting the victim or to apply mouth-to-mouth resuscitation (one man rescue), the rescuer will not lose time in reapplying CPR because the device will have remained in the proper position on the patient's chest. Further, the chance of causing damage by inadvertently applying pressure or force in the wrong place will be greatly reduced.

Any type of suitable pressure or force sensing device coupled with a suitable pressure or force indicating means may be employed in the practice of this invention. For example, an electrical transducer might be used to sense pressure in the inflatable cushion or might be used to sense direct pressure applied by the rescuer to the patient without the use of a cushion. Pressure or force indicating means may be a visual, audible or even a tactile signal to notify the rescuer that the proper pressure or force has been reached.

Additional embodiments of the invention provide devices for measuring and indicating the amount of movement of the patient's sternum during the application of CPR. This measurement of sternum movement toward the patient's spine provides an alternative to the measurement of pressure or force applied to the sternum. The application of eighty (80) pounds to one hundred (100) pounds of pressure force to the sternum of an average adult male moves the sternum toward the spine one and one-half ($1\frac{1}{2}$) to two (2) inches. Movement beyond this distance may be dangerous to the patient and may result in broken ribs or other undesirable effects. Accordingly, an embodiment of this invention also provides for an apparatus for limiting the movement of the sternum to a predetermined maximum distance.

In another invention embodiment, the blood pressure of the patient is monitored to determine whether the application of cardiac resuscitation is adequate. This apparatus senses the patient's blood pressure above the predetermined pressure necessary to be maintained during properly applied resuscitation. If this monitored blood pressure falls below the threshold value, the rescuer can take appropriate action to improve the manner of resuscitation application.

It should be understood that both the foregoing general description and the following detailed description of the invention are exemplary and explanatory and are not restrictive of the invention.

The accompanying drawings, which are incorporated in and constitute a part of this specification, illustrates the invention, and together with the description serve to explain the principles of the invention.

FIG. 1 is a perspective view of one embodiment of this invention;

FIG. 1a is an elevation view of an alternative invention embodiment;

FIG. 2 is an elevation view, partly in section, of another embodiment of the invention;

FIG. 3 is a fragmentary section view of the embodiment shown in FIG. 2 taken along line 3—3 and looking in the direction of the arrows;

FIG. 3a is a perspctive view of one embodiment of the bellows;

FIG. 3b is a perspective view of another bellows configuration;

FIG. 3c is a fragmentary section of a portion of the embodiment shown in FIG. 3 and illustrating an insert;

FIG. 4 is a top plan view, partly in section, of a further invention embodiment;

FIG. 4a is an elevation view of the embodiment shown in FIG. 4 with a portion shown in section;

FIG. 5 is a top plan view, partly in section, of another embodiment of the invention;

FIG. 5a is an elevation view of the embodiment illustrated in FIG. 5 with a portion in section;

FIG. 6 is an elevation view of another invention embodiment, partly in section;

FIG. 7 is a top plan view, partly in section, of the embodiment shown in FIG. 6;

FIG. 8 is a top plan view, partly in section, of another embodiment of the invention;

FIG. 9 is an elevation view, partly in section, of the embodiment shown in FIG. 8;

FIG. 10 is a top plan view, partly in section and partly fragmentary, of still a further invention embodiment;

FIG. 11 is an elevation view, partly in section of the FIG. 10 embodiment;

FIG. 12 is an elevation view, partly in section, of another invention embodiment;

FIG. 13 is an elevation view, partly in section, of another embodiment of the invention and showing a patient positioned in relation to this embodiment;

FIG. 14 is a diagrammatic view of still a further invention configuration;

FIG. 15 is a diagrammatic illustration of another embodiment of this invention;

FIG. 16 is a diagrammatic section view of a further invention embodiment;

FIG. 17 is a digrammatic view of a portion of the embodiment shown in FIG. 16;

FIG. 18 is a diagrammatic elevation view of another invention embodiment;

FIG. 19 is a top plan view of the embodiment shown in FIG. 18;

FIG. 20 is a diagrammatic elevation view of still a further invention configuration;

FIG. 21 is a diagrammatic elevation partly in section, of another embodiment of this invention;

FIG. 22 shows the embodiment of FIG. 21 when the patient's chest is being compressed;

FIG. 23 shows a top plan view of an alternative embodiment to FIGS. 21 and 22;

FIG. 24 is a diagrammatic elevation view of still another invention embodiment;

FIG. 25 is a fragmentary top plan view of the embodiment shown in FIG. 24;

FIG. 26 is a perspective view of the embodiment illustrated in FIGS. 24 and 25;

FIG. 27 is a diagrammatic elevation view of a further invention embodiment;

FIG. 28 is a fragmentary perspective view of a portion of the embodiment shown in FIG. 27.

FIG. 29 is an elevation view of another invention embodiment;

FIG. 30 is a perspective view of the embodiment of FIG. 29;

FIG. 31 is an elevation view of still an additional embodiment of this invention;

FIG. 32 is a top view of the embodiment shown in FIG. 31;

FIG. 33 is a perspective view of another invention configuration;

FIG. 34 is a top view of the invention configuration of FIG. 33; and

FIG. 35 is a perspective view of still another invention embodiment.

With reference now to the drawings, wherein like reference characters designate like or corresponding parts throughout the several views, there is shown in FIGS. 1-3 apparatus for use by a rescuer in administering cardiopulmonary resuscitation to a patient or for use as a training aid in the application of cardiopulmonary resuscitation including means 100 for receiving manually applied force or pressure and wherein means 100 includes means 102 for distributing the manually applied force or pressure over a predetermined area. Specifically, pressure or force distributing means 102 includes an inflatable, walled cushion 104 defining a first inner chamber 106 and a second inner chamber 108 interconnected with first chamber 106 and in fluid communication therewith by means of passageway 110. Inflation means 112, which may include a one-way inflation valve (not shown) and an inflation tube 114 attached to cushion 104, enables inflation of the cushion by introduction of air or other fluid through tube 114 and into the cushion chambers. Inner chamber 106 is preferably one and one-half inches by three inches in size and approximately one-half inch deep. This is representative of all the cushion embodiments of this invention.

Pressure or force sensing means 116 are provided in operative relationship with pressure or force receiving means 100 for sensing force or pressure applied to receiving means 100. Pressure sensing means 116 includes a third inflatable walled chamber 118 located within second chamber 108 and defining a passageway 120 in fluid communication with the interior of third chamber 118 and the ambient atmosphere.

Means 122 are provided in operative relationship with pressure sensing means 116 for indicating the pressure or force applied to pressure receiving means 100. More particularly, pressure or force indicating means 122 include indicia 124 on the wall 126 of the cushion and on the wall 128 of third chamber 118.

Wall 128 preferably defines a plurality of normally extended accordion-like elastic pleats 130 for enabling movement of indicium 124 along a substantially linear path when third chamber 118 is expanded and contracted. As shown in more detail in FIG. 3a, pleats 130 define two opposing and substantially parallel walls 132, and two additional planar and substantially parallel walls 134 extend between pleated walls 132. Alternatively; pleats 130 may extend completely around third chamber 118 to enable easy expansion and contraction thereof. This configuration is illustrated in FIG. 3b.

It may be desirable to control the rate of air flow through passageway 120. For example, if a two-man rescue operation is being performed upon a patient, a slower cycle of application and release of pressure or force to the patient's chest is preferred than the cycle used for a one-man rescue operation. Therefore, means 136, shown in FIG. 3c, is located in operative relationship with passageway 120 for reducing the rate of air flow through the passageway and for enabling an increase in the rate of flow of air therethrough when insert 136 is removed from the passageway. Insert 136 includes a flexible flanged end portion 138 and a tubular portion 140 defining an axial passageway 142. A handle member 144 is also attached to tubular portion 140 to enable easy insertion and removal of insert 136 with respect to passageway 120. Flexible end portion 138 will bend when the insert is pulled outwardly by means of handle 144. Conversely, end portion 138 can be compressed to enable insertion of insert 136 into passageway 120, and end portion 138 will expand to normally retain insert 136 within passageway 120.

The constricted passageway 142 of the insert slows the ingress and egress of air with respect to third chamber 118 and provides the slower resuscitation cycle desirable for a two-man rescue operation. When insert 136 is removed, however, the rate of ingress and egress of air with respect to chamber 118 is increased and provides the desired resuscitation cycle for one-man rescue. Of course, various other arrangements could be used for controlling the rate of air flow through passageway 120. One such arrangement might be an adjustable valve, an adjustable needle valve or the use of any other device to predictably vary the rate of air flow through passageway 120 during expansion and contraction of chamber 118.

Pressure or force receiving means 100 also preferably includes a rigid member 146 having a flat, platelike configuration and attached to cushion 104. Rigid member 146 is attached to cushion 104 by means of first and second pieces of tape 148, 150 having adhesive 148', 150' applied to one side only of each of the tape pieces. Each of the tape pieces has a portion of the adhesive side attached to cushion 104 and a remaining portion of the adhesive side attached to platelike member 146. Rigid member 146 acts to enchance even distribution of the forces applied by the rescuer and acts in cooperation with resilient cushion 104 to evenly distribute those forces over the sternum area of the patient's chest.

Cushion 104 also preferably includes means 152 for preventing sliding movement of the cushion with respect to the patient's chest. Means 152 may include an adhesive applied to the bottom surface 154 of the cushion, or alternatively, means 152 may include a plurality of suction cups 152' attached to surface 154 for holding cushion 104 in a fixed position relative to the patient's chest. This embodiment is illustrated in FIG. 1a. If adhesive is applied to bottom surface 154 of the cushion, it is preferable that a sheet 156 (FIG. 2) be removably attached to and cover the adhesive thereby preventing undesirable sticking of the adhesive when the apparatus is not in use. Alternately, means 152 may merely include a roughening of surface 154 so that sliding movement of the cushion on the patient's chest is prevented.

In addition to controlling the amount of pressure applied by the rescuer to the patient's chest, it is also important to accurately control the rate at which the pressure is applied and removed. It is desirable to apply a greater force to a larger person than to a smaller individual, and it is important to vary the rhythm with respect to an adult or a child, for example. Thus, an important feature of this invention provides for the relaxation to a zero reading from various pressure readings by pressure or force indicating means 122 within varied but predetermined time intervals. Such a timing feature is incorporated into the invention illustrated in FIGS. 1-3, and timing means 158 includes constriction 160 in fluid communication with chamber 118, pleats 130 and also includes passageway 120. The collapsing movement of chamber 118, as it is compressed by the application of pressure to chambers 106 and 108, causes indicium 124 to move in a linear direction to a position adjacent to a second indicium 124 appropriate for the pressure or force applied. When pressure is reduced in chambers 106 and 108 by removal of force or pressure to the cushion by the rescuer, pleats 130 act to expand chamber 118 back to its original position, and pleats 130 act in conjunction with the in-flow of air to chamber 118 through passageway 120 and through constriction 160. Of course, indicating means 122 can be calibrated so that maximum compression of pleats 130 occurs at any desired force or pressure, such as on one hundred forty (140) pounds.

The greater the collapse of chamber 118 to indicate a greater force or pressure, the longer it takes for the chamber to reexpand to the zero position. Thus, a slower cycle or rhythm is established for the application of greater force than for the application of lower forces by the rescuer, and this is precisely the timing relationship required for adequate resuscitation of adults and children. For example, if chamber 118 is compressed so that indicium 124 on wall 128 is moved from the zero position to a position indicating a force of ninety (90) pounds, pleats 130 will be compressed. When pressure is reduced in chamber 106 and 108 by removal of the rescuer's weight from the cushion, pleats 130 together with the return of air into chamber 118 act to move indicium 124 back to its zero position. Conversely, if a lesser pressure or force is originally applied by the rescuer to chambers 106 and 108, and indicium 124 is moved a shorter distance to a position adjacent to a pressure force indication of sixty (60) pounds, for example, indicium 124 will have a shorter path to travel back to the zero position and it will return to zero in a shorter time than it takes to return to zero from a reading of ninety (90) pounds. Accordingly, not only can the correct pressure or force applied to the patient's chest be controlled but also the proper rhythm for any patient may also be maintained.

Another feature of this embodiment of the invention provides for a pressure relief valve 162 in fluid communication with chamber 106 whereby valve 162 will act to release pressure from chamber 106 in the event the pressure applied to that chamber by the rescuer exceeds a predetermined maximum. This has the desired effect of preventing inadvertant excessive force or pressure being applied to the patient's chest area.

Pleated chamber 118 may be positioned within cushion 104 and attached thereto in numerous ways. For example, a pocket 164 can be formed within cushion 104, and a portion 166 of chamber 118 can be positioned within pocket 164 and attached thereto by means of glue or other adhesive means 168. Alternately, cushion 104 and the walls of chamber 118 may be formed from a plastic or other material whereby portion 166 of chamber 118 can be fused or heatsealed to the interior walls of pocket 164.

Cushion 104 may also be formed of two separate pieces 170, 172 joined together by means of a heat-seal or glue along a perimeter 174.

In operation of the embodiments illustrated in FIGS. 1-3, the apparatus is positioned on the chest of the patient and directly above the lower sternum. If an adhesive layer 152 is applied to bottom surface 154 of cushion 104, sheet 156 is first removed and the adhesive is placed into direct contact with the patient's chest to cause the cushion to adhere thereto. The cushion will have been inflated via inflation tube 114 prior to this placement on the patient's chest.

With the patient positioned on his back and on a firm surface, the heel of one of the rescuer's hands is placed onto rigid member 146. The rescuer then places his other hand on top of the first. The rescuer rocks forward keeping his arms straight and using the weight of the upper portion of his body to exert eighty (80) to one hundred (100) pounds of force for an adult male. This application of force is transmitted from platelike member 146 to the air or other fluid located within chambers 106 and 108 of the cushion. The increased pressure within these chambers resulting from the application of force to platelike member 146 causes impingement of that increased pressure against wall 128 of third chamber 118. Indicium 124 or wall 128 will be positioned for a zero readout prior to any application of force by the rescuer to platelike member 146, but, the pressure applied thereto by the rescuer causes pleated chamber 118 to be compressed and air is expelled therefrom through constriction 160 and through passageway 120 to the ambient atmosphere. Indicium 124 on wall 128 continues to move until the resistance of pleated chamber 118 equalizes the increased pressure applied to wall 128. Indicia 124 will then readout the correct amount of pressure or force being applied to the cushion and to the sternum of the patient by the rescuer.

The rescuer then removes all force from rigid member 146 so that the pressure within chamber 106 and 108 of the cushion is then reduced to its normally inflated pressure. This enables pleats 130 to expand chamber 118 back to its original position in conjunction with the reentry of air into chamber 118 through passageway 120 and through constriction 160. The device is then ready for the reapplication of pressure or force and the cycle is continued.

An alternative embodiment of the invention is illustrated in FIGS. 4-4a wherein inflatable, walled cushion 104 defines first chamber 106 and second chamber 108'. Inflation tube 114, incorporating a one-way valve therein (not shown), is provided in fluid communication with chamber 106 for enabling inflation of the cushion. Pressure or force sensing means are also provided and include a third inflatable, walled chamber 118' located within second chamber 108 and in fluid communication, via passageway 176, with chamber 106. The pressure or force indicating means also include indicia 124 positioned on the wall of cushion 104 and on the wall 128' of third chamber 118'.

As in the previously described embodiments, wall 128' of chamber 118' defines a plurality of accordion-like, elastic pleats 130 for enabling movement of indicium 124 positioned on wall 128' along a substantially linear path when chamber 118' is expanded and contracted. Means are also provided in operative relationship with chambers 106 and 118' for controlling the rate of air flow therebetween, and this controlling means includes a fixed or adjustable constriction 178 located within passageway 176 between chambers 106 and 118'. An adjustable needle valve or any other adjustable device (not shown) may be used to vary the amount of constriction and to control the rate of air flow between the chambers.

In addition, rigid, flat, platelike member 146 is attached to cushion 104 in continuous relationship with chamber 106. This rigid member may be attached to the cushion in the manner described with respect to the preceding embodiment, and it acts to enhance even distribution of pressure or force as previously described. This embodiment may also include means 154 associated with cushion 104 for preventing sliding movement of the cushion relative to the patient's chest. This movement preventing means may include a roughened lower wall, a plurality of suction cups positioned on the lower wall of the cushion, or an adhesive 155 attached to the lower wall of the cushion and protected by a removable sheet 156.

An important feature of this embodiment also provides for timing means 158' for enabling expanded chamber 118' to relax from any pressure or force reading to a zero reading within predetermined time intervals when pressure force is removed by the rescuer from platelike member 146. This timing feature is effected by means of the cooperative relationship between elastic pleats 130 and constriction 178 whereby pressure or force applied by the rescuer to rigid member 146 is transmitted to chamber 106 and into chamber 118' via constriction 178. This increase of pressure within chamber 118 causes the chamber to expand until indicia 124 read out the pressure or force applied. When force is removed by the rescuer from member 146, the pressure within chambers 106 and 118' is reduced so as to enable elastic pleats 130 to retract, and indicia 124 return to a zero readout. If chamber 118' is expanded to a great extent as a result of a large pressure or force applied by the rescuer, indicium 124 on wall 128' moves a great distance to indicate the pressure or force. Return of indicium 124 to a zero reading from this high reading requires a greater time interval than does its return to zero from a smaller reading. Thus, a slower cycle or rhythm is established for application of greater pressures or force than for the application of lower pressures or force by the rescuer, and the proper timing is achieved for proper resuscitation of all sizes of persons.

An alternative embodiment of the invention is illustrated in FIGS. 5-5a wherein means are provided in operative relationship with first chamber 106 for sensing the average maximum pressure applied by the rescuer to chamber 106 and wherein pressure or force indicating means are provided in operative relationship with the average maximum pressure sensing means for indicating the average maximum pressure or force applied by the rescuer to chamber 106. Specifically, cushion 104 defines a fourth chamber 180 within the cushion, and the average maximum pressure sensing means includes a fifth, inflatable, walled chamber 182 located within chamber 180 and in fluid communication with chamber 106 via passageway 107. Further, the average maximum pressure or force indicating means includes second indicia 124' positioned on the wall of cushion 104 and on the wall 184 of chamber 182.

Wall 184 defines a plurality of accordion-like elastic pleats 130' for enabling movement of indicium 124' located on wall 184 along a substantially linear path when chamber 182 is expanded and contracted. A very tight constriction 178', that may be fixed or variable, is located between chamber 182 and chamber 106 for controlling the rate of air flow therebetween. Because constriction 178' is very small, the rate of air flow therethrough is such that only a relatively small volume of air passes through the constriction during any relatively short time period. Accordingly, when pressure or force is applied to chamber 106 and is transmitted to chamber 182, chamber 182 slowly expands so that the indicia will ultimately indicate the maximum pressure or force applied to chamber 106. However, when pressure or force is removed from chamber 106, constriction 178' prevents any great amount of air from moving back into chamber 106 from collapsible chamber 182, and the effect is for indicia 124' to provide a substantially constant readout of the maximum pressure or force applied to chamber 106 and to the chest of the patient. In fact, the average maximum pressure or force so applied is indicated by means of indicia 124'.

Flat rigid member 146 is preferably attached to cushion 104 in contiguous relationship with chamber 106 for enchancing even distribution of force or pressure applied by the rescuer. Means 152 may also be used, as in previously described embodiments, for preventing sliding movement of cushion 104 with respect to the patient's chest. This may include adhesive or suction cups, for example.

Another embodiment of the invention is illustrated in FIGS. 6-7 wherein a force or pressure distributing means 102' includes an inflatable cushion 186 defining a first chamber 188 within the cushion, and means 190, such as an inflation tube, are provided in operative relationship with cushion 186 for enabling inflation of chamber 188. A one-way valve (not shown) may be used together with inflation tube 190 for permitting air to pass into chamber 188 but not to exit therefrom through tube 190.

A pressure or force sensing means 192 includes a second normally coiled walled chamber 194 in fluid communication with first chamber 188 whereby the application of increasing increments of force or air pressure by the rescuer to chamber 188 causes corresponding increases in pressure within chamber 194. This, in turn, causes chamber 194 to uncoil from its normally coiled position in predetermined increments to display indicia 200 indicating that the correct amount of force or pressure is being applied to the patient.

Normally coiled second chamber 194 defines an inner wall 196 and an outer wall 198, and indicia 200 are located on inner wall 196 so as to be sequentially exposed to view as chamber 194 uncoils with increased application of air pressure to the interior thereof. It is preferable that means 202 be provided between first chamber 188 and second chamber 194 for controlling the rate of air flow therebetween. Controlling member 202 may be a fixed or variable constriction as desired. If variable, a needle valve or other similar arrangement (not shown) may be used.

As in the preceding embodiments, a rigid, flat, plate-like member 146 is preferably attached to cushion 186 in contiguous relationship with chamber 188. In addition, means 152 are preferably provided on the bottom surface 154 of cushion 186 for preventing sliding movement of the cushion relative to the patient's chest. Sliding preventing means 152 may include an adhesive layer or a plurality of suction cups, as described with respect to the previous embodiments, and if an adhesive layer 155 is used it is preferable to provide a removable sheet 156 to normally cover the adhesive layer.

In operation of this embodiment, cushion 186 is placed onto the patient's chest and over the sternum of the patient. Pressure or force is applied by the rescuer to rigid plate 146, and this is, in turn, transmitted via the air pressure within chamber 188 to the interior of second chamber 194. Walls 196, 198 of chamber 194 are treated so that they normally are in a coiled position and indicia 200 are normally hidden from view. As the air pressure within chamber 194 is increased with the increased application of force by the rescuer to plate 146, the walls of chamber 194 are gradually uncoiled so as to expose indicia 200. Air flow control member 202 and the normal pressure within chamber 188 are such that appropriate indicia (infant, child, woman or man) are exposed to the rescuer's view when the proper force is being applied to the patient's chest.

For example, if resuscitation is being applied to a child, relatively less force is required than for adults and chamber 194 will uncoil to expose the indicia "child" when that lower required pressure or force is reached. On the other hand, if resuscitation is being applied to an adult male a greater amount of force is required and chamber 194 will uncoil to expose the indicia "man" to the rescuer when that appropriately greater force or pressure is applied. Thus, a simple and accurate determination and control of the amount of pressure or force being applied to the patient is provided by use of this embodiment.

A further embodiment of this invention is illustrated in FIGS. 8-9 wherein pressure or force distributing means 102 includes a cushion 204 defining a chamber 206, and pressure or force sensing means 116 includes a capillary tube 208 in liquid communication with chamber 206. A liquid, preferably colored to enhance visibility, fills chamber 206, and capillary tube 208 is also normally partially filled with the colored liquid 210 to a predetermined location. Indicia 212 are positioned adjacent to capillary tube 208 and act in conjunction with the liquid in the tube to indicate to the rescuer the pressure or force applied to cushion 204. Liquid 210 normally extends into capillary tube 208 to a position adjacent to the zero indicium.

If desired, a chamber 214 may be provided in fluid communication with capillary tube 208, and chamber 214 may be filled with air or other suitable material for controllably opposing movement of colored liquid 210 within the capillary tube. In addition, a cover 216 may be positioned over chamber 214 so that only capillary tube 208 and the indicia are exposed to the rescuer's view.

It may also be desirable to provide means 218 between chamber 206 and capillary tube 208 for controlling the rate of liquid flow therebetween. Flow control 218 may be fixed or adjustable, as desired. If adjustable, a needle valve or other similar arrangement (not shown) may be used for varying the amount of constriction. A fixed "snubber" screw (not shown) having a hollowed out axial portion may also be used. The screw would be placed coaxially within passage 219 and would operate to control the rate of liquid flow and to prevent undesirable fluctuation in pressure within the liquid. This feature may be used in each of the embodiments of this invention where constriction of fluid flow is desired. The "snubber" screw serves the dual purpose in this invention of timing movement of the pressure gauge pointer and of preventing undesirable fluctuations in fluid pressure.

As in the preceding embodiments, a rigid, flat, plate-like member 146 may be attached to cushion 204 and in contiguous relationship with chamber 206 for enhancing even distribution of force and pressure to the colored liquid and ultimately to the patient's chest. Furthermore, means 152 may be provided on the bottom surface 154 of cushion 204 for preventing movement of the cushion relative to the patient's chest. This may include an adhesive layer, a plurality of suction cups or merely a roughened surface 155. If an adhesive layer is provided it may be desirable to provide a removable sheet 156 to normally cover the adhesive surface.

In operation of the embodiment illustrated in FIGS. 8-9, cushion 204 is placed onto the patient's chest and over the sternum area. Force is then applied by the rescuer to rigid plate 146, and this force is transmitted through colored liquid 210 to the sternum of the patient. In addition, the pressure and force applied to chamber 206 and to the liquid causes the liquid to move within capillary tube 208 from the zero position to a position adjacent to the appropriate pressure or force reading. This movement of the liquid within capillary tube 208 compresses the air or other gas within reservoir chamber 214 or merely within the end portion 220 of the capillary tube if no such reservoir chamber is used.

When force is released from plate member 146 and from the liquid, the compressed air or other gas within reservoir chamber 214 or within the end portion 220 of the capillary tube forces the colored liquid back to the zero position with the excess of the liquid returning to chamber 206.

Because the timing of the application and release of pressure or force by the rescuer is very important to achieve proper blood circulation in the patient, the speed with which the liquid moves within the capillary tube to indicate the desired pressures is important. Accordingly, a flow controlling member 218 provides a constriction between the capillary tube and chamber 206, and this constriction may be adjustable to accurately control movement of the liquid. If the return of the liquid from the tube into chamber 206 is properly controlled, the rescuer will be able to apply the appropriate pressure or force until the liquid moves to the indicium appropriate for that pressure or force. The rescuer can then remove all application of pressure or force until the liquid position within the capillary tube returns to the zero reading. The rescuer will then know to immediately reapply force to rigid plate 146 and the process can be repeated. In addition, it requires a longer time interval for the liquid to return to zero from a higher pressure or force reading than it does from a lower reading. Thus, proper timing of application and release of pressure or force is provided for all persons if the rescuer applies force until the appropriate reading is reached and then releases all force until a zero reading is reached.

FIGS. 10–11 illustrate another embodiment of the invention adapted for properly timing lung ventilation with the application of force to the patient's chest. Where resuscitation is being applied by a single rescuer, it is desirable that the patient's lungs be ventilated by means of mouth-to-mouth resuscitation every fifteen (15) cycles of compression and release of force to the patient's chest. similarly, where a two-man rescue operation is being performed, it is desirable that lung ventilation be provided once for every five (5) cycles of chest compression and release.

The apparatus illustrated in FIGS. 10–11 provides for the counting of the number of pressure or force-release cycles applied to the patient's chest and also incorporates means for indicating this count to the rescuer or rescuers.

More specifically, means 100 is provided for receiving manually applied pressure or force and for evenly distributing the force and pressure over the sternum area of a patient. Means 100 may include a cushion 222 defining a chamber 224 in fluid communication with pressure or force indicating means 122. Means 122 may include a pressure gauge 226 incorporating a counting means 228 for counting the number of times the pressure gauge is operative to indicate a predetermined minimum pressure or force from a zero reading. Counting means 228 preferably includes a movable blind 230 having an aperture 232 therein. Indicium 234 is positioned on the pressure gauge and beneath blind 230 for periodic alignment with aperture 232 as the blind is rotated about axis 236.

Means 238 are also provided in operative relationship with pointer 240 of the pressure gauge for moving blind 230 about axis 236, and means 238 includes a disc 242 rotatable about axis 236 and having a first plurality of projections 244 thereon. A second projection means 246 is attached to pointer 240 and is positioned for engaging one of projections 244 each time pointer 240 moves from a zero reading to a second and greater predetermined reading.

Projection 246 preferably comprises a spring loaded ratchet arrangement (details not shown) whereby projection 246 will slide over projections 244 without fixedly engaging those projections when the pointer is moving toward a zero reading in a counterclockwise direction. When pointer 240 moves from a zero reading to a greater pressure or force reading, and in a clockwise direction as illustrated, projection 246 will fixedly engage one of projections 244 so as to move blind 230 about axis 236 in a clockwise direction during at least a portion of the movement of pointer 240.

Thus, projections 244 may be spaced in such a manner that blind 230 will cover indicium 234 except after every fifth application of predetermined pressure or force by one rescuer to the patient and after every fifth movement of pointer 240 from a zero reading to a predetermined force or pressure reading indicating the force or pressure applied by the rescuer. After every fifth cycle of pressure application and release by one rescuer, aperture 232 will be positioned above indicium 234 to enable the rescuers to view the indicium. This will indicate to the rescuers that it is time to apply lung ventilation. Of course, the spacing of projections 244 on disc 242 can be varied to provide for any desired timing sequence. In fact, disc 242 may be interchangeable with other discs (not shown) having projections spaced at different intervals so that the apparatus of this invention can be adaptable for use by one-man or two-man rescue operations and for use for the application of different maximum forces or pressures.

The embodiment shown in FIG. 10 may also be provided with a spring-loaded, self-indexing cam system as a part of counting means 228, whereby each disc 242 is provided with an irregular cam surface 243. A spring-loaded cam follower 245 is positioned adjacent to surface 243 and in spring-biased, contacting relationship with the surface. This arrangement ensures that disc 242 will rotate exactly one-fifth of a complete rotation if a predetermined minimum force, e.g. 30 pounds, is applied to pressure or force receiving means 100.

Projections 244 may be provided in sufficient number and spacing so that the application of a predetermined minimum pressure or force to means 100 causes disc 242 to rotate through an arc to cause follower 245 to ride up from its normally stable position in groove 247 to land 249. Even if the minimum force applied is not enough to cause disc 242 to rotate the full desired one-fifth revolution, the spring action of follower 245 against surface 243 will cause the disc to continue to rotate in a clockwise direction until follower 245 returns to the next groove 247. This automatically causes the disc to rotate the desired one-fifth revolution for each application of a predetermined minimum pressure or force to means 100, and the proper timing for lung ventilation with the application of pressure or force to the patient's chest is maintained.

If resuscitation is being applied by a single rescuer, another replaceable disc (not shown) having a different cam configuration can be used so that the disc will rotate exactly one-fifteenth of a complete revolution upon the application of a predetermined minimum pressure or force to pressure or force receiving means 100. This will enable the single rescuer to maintain the proper timing for lung ventilation with the application of force to the patient's chest.

As in the preceding embodiments, this embodiment preferably includes a flat, rigid member 146 attached to cushion 222 for enhancing even distribution of force or pressure over the patient's sternum area. In addition, means 152 are associated with cushion 222 for preventing sliding movement of the cushion on the patient's chest. Means 152 may include an adhesive layer, a plurality of suction cups or merely a roughened bottom surface 154 of the cushion. In the event an adhesive layer is used, it is preferable to provide a removable sheet 156 to normally cover the adhesive layer.

With reference now to FIG. 12, there is shown another embodiment of this invention having a resilient, walled cushion 248 defining at least a first interior chamber 250 and having a pressure gauge 252 in fluid communication with chamber 250 for indicating the pressure within the chamber. In addition, two rigid members 254, 256 are positioned one above and one below cushion 248, and resilient, compressible, support members 258, 260 are positioned between the rigid members for maintaining the rigid members in normally spaced relationship from each other while permitting movement of the rigid members toward one another upon the application of pressure or force thereto. Support members 258, 260 are preferably attached in some conventional manner to rigid members 254, 256, and a second cushion member 262 is attached to rigid member 256 for cushioning and evenly distributing forces applied by the rescuer to the patient's chest. A third cushion 264 is also attached to rigid member 254 for cushioning the hands of the rescuer.

In operation of the embodiment illustrated in FIG. 12, the apparatus is placed onto the patient's chest with cushion member 262 positioned directly over the sternum area. Pressure or force is then applied by the rescuer to cushion member 264, and this force causes support members 258, 260 to compress. Rigid members 254, 256 cause the air or other fluid within chamber 250 to compress and to cause a reading to be registered on pressure gauge 252. Support members 258, 260 are resilient so that when force is released by the rescuer these supports return to their normal position and permit cushion 248 to expand to its original shape. This, in turn, results in a reduction of pressure within chamber 250, and the pressure reduction is registered as a zero reading by pressure gauge 252. The process then repeats this cycle.

It may also be desirable to provide means 152 on the bottom surface of cushion 262 for preventing sliding of the apparatus on the patient's chest. As in the previously described embodiments, means 154 may include an adhesive layer, a plurality of suction cups or merely a roughened surface 154. A removable sheet 156 may also be desirable if an adhesive layer is used to normally cover the adhesive layer until time for placement of the apparatus onto the patient's chest.

Another embodiment of this invention is illustrated in FIG. 13 wherein the apparatus is particularly adapted for placement beneath the patient. Specifically, rigid members 266, 268 are attached to and positioned on opposite sides of a resilient cushion 270, having an interior chamber 271 therein. Members 266, 268 are flat, platelike members, and a pressure gauge 272 is connected to cushion 270 and in fluid communication with chamber 271 for indicating the pressure or force applied thereto. Gauge 272 is adjustable so that it may be set to zero after the patient has been positioned on top of the cushion. Pressure or force applied by the rescuer directly to the patient's chest is transmitted to the pressure gauge via the air or other fluid within chamber 271.

Another embodiment of the invention for enabling monitoring of the patient's blood pressure during application of cardiopulmonary resuscitation and for aiding in diagnosis of cardiac arrest is illustrated in FIG. 14.

As illustrated, means 274 are attached to pressure or force receiving means 100 for measuring and indicating the blood pressure of the patient during administration of resuscitation so that the effectiveness of the resuscitation can be determined and so that any restoration of the patient's heart beat can be determined during momentary interruption of the administration of resuscitation.

The invention also comtemplates that means 274 could include any blood pressure readout device and/or blood flow measuring device, such as a Doppler effect blood flow device. Specifically, means 274, as illustrated, includes a blood pressure gauge 276 attached to pressure or force receiving means 100, a tube 278 extending from gauge 276 to a walled chamber 280. A cuff or wrapping 282 is attached to chamber 280 for positioning the chamber against an extremity 284 of the patient and for holding the chamber in position. A branch tube 286 extends from tube 278 and leads to a bellows or bulb member 288 having a valve 290 therein for enabling movement of air into the bulb only. A release valve 292 is also positioned with respect to branch tube 286 for releasing the buildup of air pressure within the tube and within chamber 280 when necessary.

By use of this embodiment of the invention it is possible to measure the patient's blood pressure above a predetermined minimum to determine if the resuscitation efforts are effective. Chamber 280 may be inflated to a pressure equal to a normal diastolic pressure of 60-80 mm. of mercury. Needle fluctuations on pressure gauge 276 will then occur only if compression of the patient's heart by the rescuer results in a blood pressure above the normal diastolic pressure. If the pressure gauge does not display pressures above the minimum, the rescuer will know that greater force must be applied to pressure or force receiving means 100, that means 100 should be repositioned or that other corrective measures must be taken in order to achieve the desired blood pressure in the patient.

An alternative embodiment is illustrated in FIG. 15 wherein chamber 280 is pressurized to sense the patient's blood pressure above a predetermined value. Protective means or cover 294 is positioned between supporting surface 296 and chamber 280 for preventing the weight of the patient from impinging upon chamber 280. Thus, the pressure applied to chamber 280 will reflect only the patient's blood pressure and will be unaffected by inaccuracy otherwise caused by the weight of the patient's extremity squeezing chamber 280 between the extremity and supporting surface 296. Cover 294 need only extend around the lower portion of the patient's extremity, but the cover must be of sufficient depth to prevent contact of chamber 280 with either the cover or with supporting surface 296.

This embodiment of the invention also uses a conventional blood pressure measuring apparatus 298 positioned on the patient's extremity 284 between chamber 280 and the patient's heart. Pressure within chamber 280' is created by means of bulb 288' and the pressure is read out by means of gauge 276'.

The objective of this embodiment of the invention is to enable measurement of the patient's blood pressure on gauge 276 only when the patient's blood pressure exceeds a predetermined level. For example, to be effective external cardiac compression should produce a systolic blood pressure of 80 mm Hg or higher. Cardiac output is approximately one-third to one-half of normal at this pressure but this usually results in a palpable carotid pulse. Thus, chamber 280' may be pressurized to approximately 80 mm Hg so that any pressure above that level created by the cardiac pressure or force applied by the rescuer will be sensed by chamber 280 and indicated by gauge 276. Any blood pressure below 80 mm Hg, of course, would not be sensed by chamber 280 or indicated by gauge 276 in view of the fact that chamber 280' is pressurized to a value of 80 mm Hg. Therefore, the rescuer need only observe gauge 276 as he applies and releases cardiac pressure to determine whether the resuscitation efforts are sufficient to produce the required minimum blood pressure in the patient.

Another embodiment of the invention is illustrated in FIGS. 16-17 wherein a substantially flat, rigid member 300 defines a centrally located aperture 302. Member 300 is of an appropriate size to be placed onto the rib cage 304 of the patient as he lies on his back. A shaft 306 extends through aperture 302, and a handle 308 is affixed to a first end of the shaft. Guides 310 may be affixed to member 300 and positioned adjacent to aperture 302 for slideably engaging and guiding shaft 306 within the aperture.

A pad or other pressure or force distributing device 312 is attached to a second end of shaft 306 for contacting the sternum area 14 of the patient's chest. A stop member 316 may also be adjustably positioned on the shaft for contacting guides 310 when the shaft is extended through aperture 302 a predetermined distance. Shaft 306 defines a plurality of threaded grooves 318 and stop member 316 preferably defines an interior aperture 320 having a plurality of grooves 322 therein for threadedly engaging grooves 318 of the shaft. Thus, the stop member may be moved to any desired position along the shaft, and a retaining member or spring 324 may be positioned around the shaft and between a retainer 326 on the shaft and the bottom surface 315 of step member 316 for maintaining the stop member in a predetermined desired location along the shaft.

In order to indicate to the rescuer that stop member 316 has contacted guides 310, it is desirable to provide a means by which this can be readily communicated to the rescuer. Specifically, an electrical contact or switch 328 (FIG. 17) is positioned with respect to a guide 310 so that when stop member 316 contacts the guide member it also acts to close contact 328. An electrical circuit is then energized to result in the illumination of an indicating lamp or activation of an audible signaling or other device 330.

An electrical energy source or battery 332 is connected in circuit with lamp 330 and with contact 328 for causing the lamp to be illuminated or the audible signaling device to be energized when contact 328 is moved to touch terminal 334.

In operation of the embodment of this invention shown in FIGS. 16-17, the patient is positioned on his back on a firm surface, and flat, rigid member 300 is placed onto the rib cage 304 of the patient with pad 312 contacting the sternum. It is known that for external cardiac compression to be effective the sternum should be moved toward the spine from one and one-half (1 ½) to two (2) inches. Member 300 is used as a reference point, and stop member 316 is adjusted along shaft 306 to a location two (2) inches above guides 310 when pad 312 is lightly resting on the patient's sternum. Grooves 318, 322 and retaining spring 324 act to hold the stop member in this desired position during the application of external cardiac compression.

The rescuer places his hands onto handle 308 and exerts a downward pressure. This results in pad 312 moving against the sternum and causing the sternum to move toward the spine for a distance of approximately two inches until stop member 316 contacts guides 310. Contact 328 is moved by stop member 316 into closed circuit relationship with terminal 334, and battery 332 causes lamp 330 to be illuminated. The rescuer upon seeing the lamp lighted knows that movement of the patient's sternum the desired distance has been accomplished and that force should be removed from handle 308.

When the rescuer releases force from handle 308, force is simultaneously released from the patient's sternum so as to permit the sternum to return to its normal position. Pad 312, however, will remain in contact with the sternum so as to facilitate immediate reapplication of force by the rescuer.

Another embodiment of the invention is illustrated in FIGS. 18-19 wherein force receiving means or cushion 336 is provided with a flat, rigid member 338 attached to the cushion. Attached to member 338 by means of hinges 340, 340' are arm members 342, 242'. Stop members 344, 344' are provided for limiting movement of arm members 342, 342', and pads 346, 346' are attached to the ends of the arm members for contacting the ribs 347 of the patient. Stop members 344, 344' may include extentions of arm members 342, 342' whereby the extensions contact rigid member 338 when the arm members are rotated to predetermined positions. This contact by extensions 344, 344' with rigid member 338 prevents further movement of the arm members. Optionally, stop members 344, 344' may be features of hinges 340, 340' which only permit movement of the hinges through a predetermined arc.

In operation of the embodiment shown in FIGS. 18-19, cushion 336 is placed onto the patient's chest and over the sternum. Pads 346, 346' fall into contact with the patient's rib cage. The rescuer then applies force to rigid member 338, and this force is distributed through member 338 and by means of cushion 336 over the sternum of the patient. Application of force also moves the sternum toward the patient's spine from one and one-half (1 ½) to two (2) inches. Pads 346, 346' continue to ride on the patient's rib cage so that arm members 342, 342' rotate about the hinges as cushion 336 is depressed. Engagement of stop members 344, 344' with rigid member 338, for example, acts to prohibit any further rotation of the arm members and causes the arm members to resist any further depression of the cushion by the rescuer. Thus, further injury or damage to the patient as a result of the exertion of excessive force is avoided, but the rescuer is assured that the compression is adequate to move the sternum the desired amount.

An alternative embodiment is illustrated in FIG. 20 wherein rigid member 338' is attached to cushion 336' and wherein limiting means 348, 348' in the form of fixed extensions from rigid member 338' limit the depression of the patient's sternum in the manner described with respect to the preceding embodiment. Pads 350, 350' are attached to extension 348, 348' and the extensions are shaped so that the pads do not contact the patient's rib cage when cushion 336' is positioned on the patient's chest without the application of force thereto. The shape of extensions 348, 348' is such that pads 350, 350' will contact the patient's rib cage only when cushion 336' has been depressed, and the patient's sternum therewith, toward the patient's spine by a distance of one and one-half (1 ½) to two (2) inches. When this limit of compression occurs, extensions 348, 348' and pads 350, 350' contact the patient's rib cage to resist further compression of the cushion.

A further embodiment of the invention is illustrated in FIGS. 21-23 wherein movement sensing means or arm members 352, 352' are rotatably attached to cushion 354 or to rigid, platelike member 356. Measuring means or projecting members 358, 358' extend from arm members 352, 352' and indicia 360 are affixed to projecting members 358, 358' for indicating to the rescuer the distance moved by the cushion and by the sternum toward the patient's spine. Indicia 360 preferably include a pointer slideably mounted on projecting member 358 so that the indicia may be adjusted to a zero reading prior to the application of pressure by the rescuer.

In operation of the embodiment illustrated in FIGS. 21-23, cushion 354 is placed onto the patient's chest and over the sternum. Arm members 352, 352' rest on the patient's rib cage 362, and pointer 360 is adjusted on projecting member 358 so that the pointer indicates a zero reading by indicia 360 located on projecting member 358' (FIG. 23). Pointer 360 is then fixedly positioned on projecting member 368 by screws or other conventional means (not shown), and the rescuer then applies force to rigid plate 356.

Experience has shown that effective external cardiac massage is provided when the patient's sternum is moved toward his spine from one and one-half (1½) to two (2) inches. This provides the proper compression of the heart to provide the necessary blood flow and blood pressure.

As force is applied by the rescuer to cushion 354 the sternum is depressed while the position of the rib cage remains essentially unchanged. As a result, arm members 352, 352' rotate about hinges 364, 364' and projecting member 358' moves beneath projecting member 358 and beneath pointer 360. As the sternum is further depressed, member 358' moves further beneath pointer 360, and indicia 360 on projecting member 358' becomes sequentially aligned with the pointer to indicate the depth of compression of the sternum. The rescuer can continue to apply force until the desired depression of the sternum, e.g. one and one-half (1½) to two (2) inches, is reached. The rescuer will then release the force from the cushion and the sternum will return to its normal position. Arm members 352 rotate about hinges 364 back to their normal position, and pointer 360 is realigned with the zero reading indicium on member 358'. This procedure can then be repeated, and the rescuer will be able to control the extent of depression of the patient's sternum so as to provide the necessary compression of the patient's heart while avoiding the possibility of further injury or damage to the patient because of excessive compression.

The configuration of arm members 352, 352' and of projecting members 358, 358' may take a number of forms. For example, FIG. 21 shows one form whereby arm members 352, 352' extend directly away from and are attached to cushion 354. Still another embodiment, illustrated in FIG. 23, shows arm members 352, 352' extending from platelike member 356. Another embodiment is illustrated in FIGS. 24-26 wherein arm members 352, 352' are attached by hinge 364 to and project from a supporting member 366 projecting from plate 356. Arm members 352, 353' may be formed with an angled portion 368, 368' so that they extend to a location approximately midway of cushion 354. Foot members 370, 370' may also be provided and these foot members may be attached to arm members 352, 352' for contacting the rib cage 353 of the patient.

Still another embodiment of this invention is illustrated in FIGS. 27-28 wherein a cushion 372 is placed onto the patient's chest 374 and wherein a rigid member 376 is attached to the cushion. An arm member 378 is hingedly attached to rigid member 376 and measuring means 380 are in operative relationship with arm member 378 for indicating the distance of movement of plate member 376 when force is applied thereto by the rescuer.

More specifically, measuring means 380 includes a support 382 mounted on a pallet 384, a hinge 386 mounted on top of support 382, adjustable pointer 388 attached to the hinge and a projecting member 390 extending from arm member 378 and having a plurality of indicia 392 thereon.

In operation of this embodiment, pallet 384 is placed under the patient's back for supporting the patient, and cushion 372 is placed onto the patient's cheat over the sternum. Pointer 388 is adjusted so as to be aligned with the zero indicium on projecting member 390. Force is then applied by the rescuer to rigid member 376, and the patient's sternum is depressed. This depression of the patient's sternum causes arm member 378 to rotate about hinge 386 and also causes corresponding movement of projecting member 390 and its associated indicia 392 with respect to pointer 388. Indicia 392 are positioned so that depression of the patient's sternum by one and one-half (1½) to two (2) inches results in the corresponding alignment of those readings by indicia 392 with pointer 383. As a result, the rescuer will be aware of the extent of depression to the patient's sternum so that the appropriate depression may be caused to occur, but excessive compression and possible injury to the patient can be avoided.

A further embodiment of the invention is shown in FIGS. 29-30. A cushion 394 is filled with air, liquid or other fluid, and pressure gauge 396 is in fluid communication with the fluid-filled interior of the cushion. A timer 398 is attached to the pressure gauge, and a timing pointer 400 extends upwardly from the timer and coaxially with a pressure gauge pointer 422. Timer 398 may be any of a number of conventional timing mechanisms, such as a metronome type timer, and the timer is provided with a first adjustment 404 for enabling the operator to control the frequency of movement of pointer 400. A second adjustment 406 is also provided on the timer for enabling the operator to control the arc that pointer 400 will pass through for each cycle of its movement.

The operator can set timer 398 to the desired frequency, e.g. 60 cycles per minute, 80 cpm, etc., to correspond to the pressure or forces-release frequency required to be administered to the patient. This is done by means of first adjustment 404. Second adjustment 406 is also set by the operator-rescuer so that pointer 400 will be displaced through an arc during each cycle so as to point to the desired pressure or force to be applied to the patient. Thus, when the timer is activated, as by switch 408, timer pointer 400 moves across the face of the pressure gauge to the desired pressure or force and at the desired frequency for optimum resuscitation results. The rescuer need only apply the amount of force to the cushion and at such a frequency that pressure gauge pointer 402 will follow the movements of the timer pointer. This will ensure that the proper force and force rhythm is applied to the patient. The timer causes the timing pointer to oscillate from a zero reading on the pressure gauge to the maximum desired force or pressure reading in the exact rhythm required, and the rescuer need only cause pointer 402 to "stay with" the timing pointer in order to provide the proper resuscitation efforts.

An additional feature of this invention is illustrated in FIGS. 31-32 wherein locater means or flap 410 extends from the bottom portion of cushion 412 for the purpose of assisting the rescuer in placing the cushion in the proper location on the patient's chest. One free edge 414 of flap 410 is arcuate in shape. The length of the flap between edge 414 and cushion 412 is such that if the rescuer places edge 414 in position immediately adjacent to the patient's xiphoid process, the cushion will automatically be in the proper position on the patient's chest for the purpose of applying force to the patient's heart through the cushion.

An alternative embodiment of the invention is shown in FIGS. 33-35 wherein a piece of planar material or tape 416 having adhesive 417 on one side thereof is arcuately shaped at one end 418 to conform substantially with the xiphoid process of the patient. A mark or marks 420 are located on the tape at a distance or distances from end 418 directing the rescuer to the proper position for applying force to the patient's heart. Thus, the rescuer can place the tape onto the patient's chest with end 418 substantially aligned with the patient's xiphoid process. Mark 420 will then show the rescuer where he should apply force in administering cardiopulmonary resuscitation. Of course, tape 416 could be provided on a roll 422 containing a plurality of identical tape sections mounted end-to-end (FIG. 35) Arcuate end 418 of each tape section could be perforated to facilitate separation of each tape section from the remainder of the tape roll. A plurality of marks 420' could also be provided to enable use on adults and children of different sizes.

The present invention provides for an important advance in the resuscitation art whereby a portable, compact, lightweight, inexpensive and sturdy apparatus enables any rescuer, whether or not trained in proper rescue techniques, to properly apply external cardiac resuscitation and/or cardiopulmonary resuscitation. The proper force and the correct timing for application and release of that force is readily achieved by use of this apparatus even when used by persons totally inexperienced in resuscitation procedures.

The invention in its broader aspects is not limited to the specific details shown and described, and departures may be made from such details without departing from the principles of the invention and without sacrificing its chief advantages.

What is claimed is:

1. Apparatus for use by a rescuer in administering cardiopulmonary resuscitation to a patient or for use as a training aid in the application of cardiopulmonary resuscitation, comprising:
   means for receiving manually applied force;
   sensing means in operative relationship with said force receiving means for sensing pressure applied to said force receiving means;
   means in operative relationship with said sensing means for indicating the force applied to said pressure receiving means;
   timing means in operative relationship with said force indicating means for enabling said force indicating means to relax from a first predetermined force reading to a second predetermined force reading during a predetermined time interval when force is removed by the rescuer from said pressure receiving means; and
   said force indicating means including a pressure gauge having a pressure gauge pointer mounted on a first axis and wherein said timing means includes a timer having a timing pointer mounted coaxially with said pressure gauge pointer.

2. Apparatus as in claim 1 wherein said timer is adjustable to control the displacement of said timing pointer and the frequency of movement of said timing pointer.

3. Apparatus as in claim 2 wherein said force receiving means include a fluid filled cushion and wherein said pressure gauge is in fluid communication with the fluid-filled interior of said cushion.

4. Apparatus as in claim 3 further include a rigid member in operative relationship with said force receiving means for enabling substantially even distribution of said forces over a predetermined area.

5. Apparatus as in claim 3 wherein said timer is attached to said pressure gauge.

6. Apparatus as in claim 5 wherein said timer includes a first adjustment control member for enabling the operator to control the frequency of movement of said timing pointer.

7. Apparatus as in claim 6 wherein said timer includes a second adjustment control member for enabling the operator to control the arc of movement of said timing pointer for each cycle of its movement.

8. Apparatus as in claim 7 wherein said timer includes a third control member for enabling the rescuer to selectively activate and deactivate said timer.

* * * * *